(12) United States Patent
Eidenshink

(10) Patent No.: US 8,403,955 B2
(45) Date of Patent: Mar. 26, 2013

(54) INFLATABLE INTRAVASCULAR FILTER

(75) Inventor: Tracee E. J. Eidenshink, Wayzata, MN (US)

(73) Assignee: Lifescreen Sciences LLC, Frisco, TX (US)

( * ) Notice: Subject to any disclaimer, the term of this patent is extended or adjusted under 35 U.S.C. 154(b) by 1457 days.

(21) Appl. No.: 10/932,679

(22) Filed: Sep. 2, 2004

(65) Prior Publication Data
US 2006/0047300 A1 Mar. 2, 2006

(51) Int. Cl.
*A61F 2/01* (2006.01)

(52) U.S. Cl. ........................................ 606/200

(58) Field of Classification Search ............... 606/200, 606/192, 194; 210/203; 604/6.09
See application file for complete search history.

(56) References Cited

U.S. PATENT DOCUMENTS

| | | | |
|---|---|---|---|
| 3,952,747 A | 4/1976 | Kimmell, Jr. | |
| 4,327,734 A * | 5/1982 | White, Jr. | 606/195 |
| 4,425,908 A | 1/1984 | Simon | |
| 4,705,517 A * | 11/1987 | DiPisa, Jr. | 606/158 |
| 4,794,928 A * | 1/1989 | Kletschka | 606/194 |
| 5,059,205 A * | 10/1991 | El-Nounou et al. | 606/200 |
| 5,108,419 A | 4/1992 | Reger et al. | |
| 5,181,921 A * | 1/1993 | Makita et al. | 606/195 |
| 5,213,576 A * | 5/1993 | Abiuso et al. | 604/103.01 |
| 5,242,462 A | 9/1993 | El-Nounou et al. | |
| 5,370,657 A | 12/1994 | Irie | |
| 5,534,024 A * | 7/1996 | Rogers et al. | 623/1.25 |
| 5,554,119 A * | 9/1996 | Harrison et al. | 604/103.01 |
| 5,662,671 A * | 9/1997 | Barbut et al. | 606/170 |
| 5,713,853 A * | 2/1998 | Clark et al. | 604/509 |
| 5,746,767 A | 5/1998 | Smith | |
| 5,769,816 A * | 6/1998 | Barbut et al. | 604/93.01 |
| 5,954,745 A * | 9/1999 | Gertler et al. | 606/200 |
| 5,984,947 A | 11/1999 | Smith | |
| 6,007,558 A | 12/1999 | Ravenscroft et al. | |
| 6,013,093 A | 1/2000 | Nott et al. | |
| 6,059,823 A | 5/2000 | Holman et al. | |
| 6,126,673 A | 10/2000 | Kim et al. | |
| 6,231,589 B1 | 5/2001 | Wessman et al. | |
| 6,245,089 B1 * | 6/2001 | Daniel et al. | 606/200 |
| 6,273,900 B1 | 8/2001 | Nott et al. | |
| 6,340,364 B2 * | 1/2002 | Kanesaka | 606/200 |
| 6,391,044 B1 | 5/2002 | Yadav et al. | |
| 6,416,530 B2 | 7/2002 | DeVries et al. | |
| 6,544,280 B1 | 4/2003 | Daniel et al. | |
| 6,551,342 B1 | 4/2003 | Shen et al. | |
| 6,558,405 B1 | 5/2003 | McInnes | |
| 6,623,507 B2 | 9/2003 | Saleh | |
| 6,706,054 B2 | 3/2004 | Wessman et al. | |
| 6,749,469 B2 | 6/2004 | Matsuoka | |
| 6,989,027 B2 * | 1/2006 | Allen et al. | 623/2.18 |
| 2001/0023369 A1 | 9/2001 | Chobotov | |
| 2003/0130688 A1 | 7/2003 | Daniel et al. | |
| 2004/0049226 A1 | 3/2004 | Keegan et al. | |
| 2004/0167564 A1 | 8/2004 | Fedie | |

* cited by examiner

FOREIGN PATENT DOCUMENTS

FR 2742650 A1 6/1997

*Primary Examiner* — Ryan Severson
(74) *Attorney, Agent, or Firm* — Seager, Tufte & Wickhem LLC (57) ABSTRACT

Inflatable intravascular filters for filtering blood clots contained within a blood vessel are disclosed. An inflatable intravascular filter in accordance with an illustrative embodiment of the present invention can include an apical head and one or more inflatable filter legs operatively coupled to the apical head. Each of the inflatable filter legs can include a first end section, a second end section, and an interior cavity adapted to receive an inflation medium for inflating and/or deflating the intravascular filter.

26 Claims, 9 Drawing Sheets

INFLATABLE INTRAVASCULAR FILTER

FIELD OF THE INVENTION

The present invention relates generally to medial devices. More specifically, the present invention pertains to inflatable intravascular filters, systems, and methods of filtering blood clots contained within a blood vessel.

BACKGROUND

Intravascular filters are used in combination with other thrombolytic agents to treat pulmonary embolism occurring within a patient. Such devices are generally inserted intravenously into a target location of the body (e.g. an artery or vein), and function by capturing blood clots (emboli) contained in the blood stream before they can reach the heart and/or lungs and cause permanent damage to the body. In the treatment of Deep Vein Thrombosis (DVT), for example, such filters can be placed in the inferior vena cava to prevent further blood clotting in the large veins of the lower body. Placement of the filter is typically accomplished percutaneously via the femoral arteries or the jugular vein using a local anesthetic, or by performing a laparotomy with the patient under general anesthesia.

There are a number of situations in which it may be desirable for a physician to remove the intravascular filter once inserted within the body. In certain circumstances, for example, the risk of pulmonary embolism may be relatively short term (e.g. about two weeks), thus requiring insertion of the device for only a short period of time. In other circumstances, it may be desirable to reposition the filter within the vessel, or to replace the existing filter with a new filter.

SUMMARY

The present invention relates to inflatable intravascular filters, systems, and methods for filtering blood clots contained within a blood vessel. An inflatable intravascular filter in accordance with an illustrative embodiment of the present invention includes an apical head and one or more inflatable filter legs actuatable between a radially collapsed (i.e. deflated) position and a radially expanded (i.e. inflated) position. Each of the inflatable filter legs can include a first end section, a second end section, and an interior cavity adapted to receive an inflation medium via an inflation catheter or other suitable fluid source. The interior cavity can be fluidly coupled to a valve mechanism disposed within the apical head to prevent the escape of inflation medium once the intravascular filter has been inflated within the blood vessel. In certain embodiments, one or more perfusion openings on the inflatable filter legs can be used to slowly weep anti-coagulant drugs and/or other therapeutic agents into the blood vessel.

In certain embodiments, the second end section of each inflatable filter leg can be coupled to or formed integrally with a base member to provide additional structural support for the intravascular filter. The base member can comprise an inflatable extension of the material forming the inflatable filter legs, or can alternatively comprise a non-inflatable member such as a wire, rod, tube, coil, or the like. In some embodiments, the base member can be configured to further bias the intravascular filter to radially expand when deployed in the blood vessel.

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
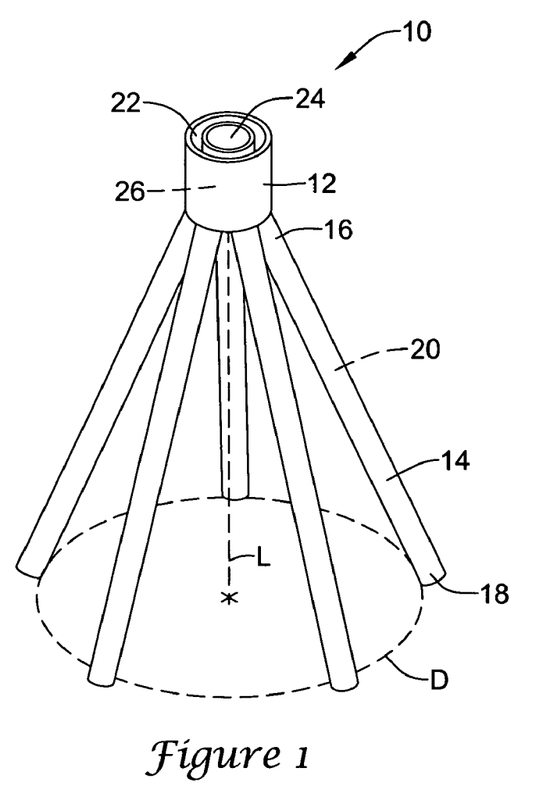
FIG. 1 is a perspective view of an inflatable intravascular.

FIG. 1 is a perspective view of an inflatable intravascular filter 10. Intravascular filter 10, illustratively a vena cava filter, includes an apical head 12 and one or more inflatable filter legs 14 actuatable between a radially collapsed (i.e. deflated) position and a radially expanded (i.e. inflated) position within a blood vessel. Each of the inflatable filter legs 14 can include a first end section 16 operatively coupled to the apical head 12, and a second end section 18 that is free to bend and/or pivot about the first end section 16. As shown in an expanded position in FIG. 1, each of the inflatable filter legs 14 can be configured identically with respect to each other, and can be symmetrically spaced about a central longitudinal axis L in a generally conical-shaped configuration. The inflatable filter legs 14 can be collectively arranged about the longitudinal axis L such that the proximal section 16 of each inflatable member 14 converges at the apical head 12 to form an apex of the intravascular filter 10.

The inflatable filter legs 14 can define an interior cavity 20 adapted to receive an inflation medium that can be used to expand the intravascular filter 10 to the shape depicted generally in FIG. 1. In certain embodiments, for example, the inflatable filter legs 14 can assume the shape of an elongated tubular member made rigid by the presence of inflation medium (e.g. saline solution) within the interior cavity 20.

The inflatable filter legs 14 can have a circular transverse cross-section as illustrated in FIG. 1, or can have some other desired shape (e.g. oval, rectangular, etc.). The interior cavity 20 may extend through all or a portion of the inflatable filter legs 14 to vary the rigidity to the intravascular filter 10, as desired.

The inflatable filter legs 14 can be formed from a suitable elastic or inelastic material configured to expand when inflated. The inflatable filter legs 14 can be biased to radially expand in an outward direction when pressurized with inflation medium, causing the inflatable filter legs 14 to exert an outwardly directed force on the wall of the blood vessel, thereby preventing the intravascular filter 10 within the blood vessel. In some embodiments, a needle, hook, barb, prong, wedge, or other attachment means can also be provided on one or more of the inflatable filter legs 14 to further prevent movement to the intravascular filter 10 therein.

The dimensions of the inflatable filter legs 14 can vary depending on the particular dimensions of the vessel in which the intravascular filter 10 is to be implanted. In applications involving implantation within the vena cava, for example, the inflatable filter legs 14 can be dimensioned to expand to a diameter D of about 18 to 32 mm, which is the normal range for the human inferior vena cava. The dimensions of the inflatable filter legs 14 can vary, however, for use in other locations within the body such as the coronary arteries or the peripheral vasculature.

The interior cavity 20 can be fluidly coupled to an annular-shaped inflation lumen 22 disposed within the apical head 12, allowing inflation medium to be injected into the inflatable filter legs 14 via the apical head 12. A guidewire lumen 24 disposed through the apical head 12 can also be provided in certain embodiments to permit the intravascular filter 10 to slide and rotate along a guidewire, if desired.

In certain embodiments, the apical head 12 can include a valve mechanism 26 configured to prevent the escape of inflation medium injected into the interior cavity 20 of the inflatable filter legs 14. The valve mechanism 26 can comprise a check valve, diaphragm valve, or other suitable one-way valve mechanism that can be used to maintain the generally rigid shape of the inflatable filter legs 14, once inflated. During retrieval of the intravascular filter 10, the valve mechanism 26 can be subsequently disengaged by the physician to deflate the inflatable filter legs 14 and collapse the intravascular filter 10, if desired.

Figure 2:
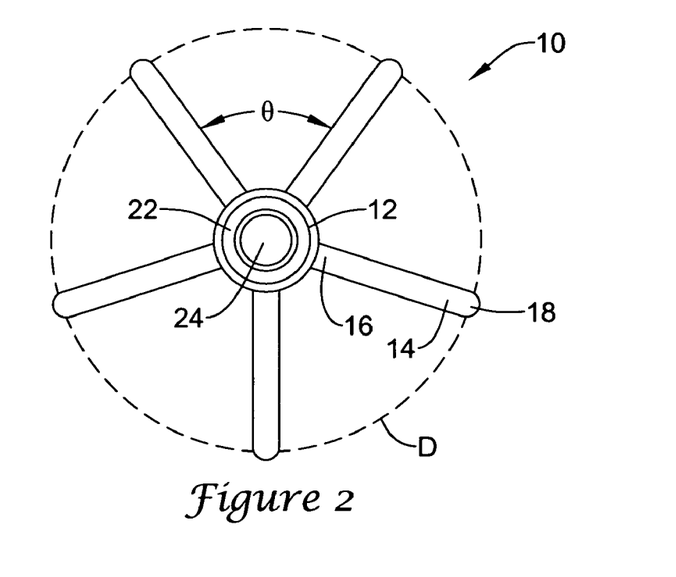
FIG. 2 is a top perspective view of the inflatable intravascular filter of FIG. 1.

FIG. 2 is a top perspective view of the intravascular filter 10 of FIG. 1. As shown in FIG. 2, the inflatable filter legs 14 can be arranged at equidistant radial intervals θ to permit the inflatable filter legs 14 to be symmetrically spaced within the blood vessel. In the illustrative embodiment of FIGS. 1-2, intravascular filter 10 is shown having five inflatable filter legs 14 spaced apart from each other at an interval θ of approximately 72°. It is to be understood, however, that any number and/or arrangement of filter legs can be employed, as desired.

When expanded within a blood vessel, the inflatable filter legs 14 provide a surface upon which blood clots (emboli) can be collected. To facilitate lysing of the collected blood clots, and to prevent the further formation of blood clots within the blood vessel, all or a portion of the inflatable filter legs 14 can be coated with or otherwise formed of a therapeutic agent. In certain embodiments, for example, the therapeutic agent can include an anti-thrombogenic and/or anti-inflammatory agent to reduce inflammation caused by the engagement of the intravascular filter 10 along the vessel wall. In some embodiments, the inflatable filter legs 14 can also include an anti-coagulant agent to prevent the further formation of blood clots within the vasculature.

Figure 3:
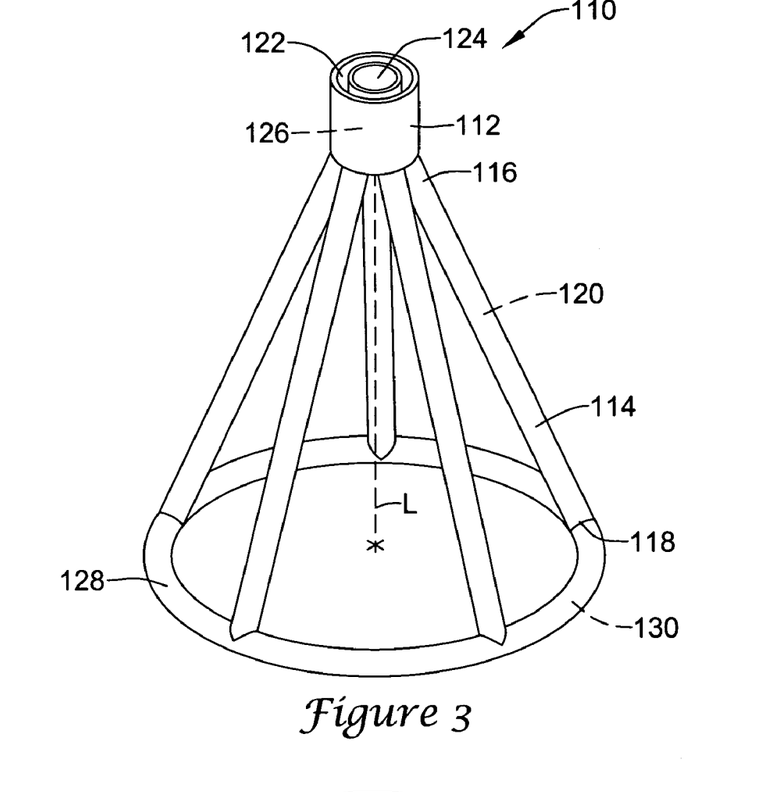
FIG. 3 is a perspective view of another inflatable intravascular filter including a base member.

FIG. 3 is a perspective view of an inflatable intravascular filter 110. Intravascular filter 110 can be configured similar to the intravascular filter 10 described above, having an apical head 112 and one or more inflatable filter legs 114 actuatable between a radially collapsed position and a radially expanded position. Each of the inflatable filter legs 114 can include a first end section 116, a second end section 118, and an interior cavity 120 at least in part therethrough adapted to receive an inflation medium. As with other embodiments herein, the apical head 112 can include other features such as an inflation lumen 122, a guidewire lumen 124, and an internal valve mechanism 126.

In the illustrative embodiment of FIG. 3, the second end section 118 of each inflatable filter leg 114 can be coupled to or formed integrally with an annular-shaped base member 128. The base member 128 can comprise an inflatable extension of the material forming the inflatable filter legs 114, or can alternatively comprise a separate member that is attached to each of the inflatable filter legs 114. As shown in the illustrative embodiment of FIG. 3, the base member 128 can comprise an inflatable member defining an interior cavity 130 in fluid communication with the interior cavity 120 of each inflatable filter leg 114. In use, the base member 128 can be configured to inflate when pressurized with an inflation medium, providing addition structural support to the intravascular filter 110. In some embodiments, the base member 128 can be configured to further bias the inflatable filter legs 114 to radially expand when deployed within the blood vessel.

While the annular-shaped base member 128 depicted in FIG. 3 comprises an inflatable member, it should be understood that other embodiments have been envisioned wherein a non-inflatable member such as a wire, rod, tube, coil, or the like is employed. As with the inflatable embodiments, each non-inflatable member can be configured to further bias the inflatable filter legs 114 to radially expand within the blood vessel.

Figure 4:
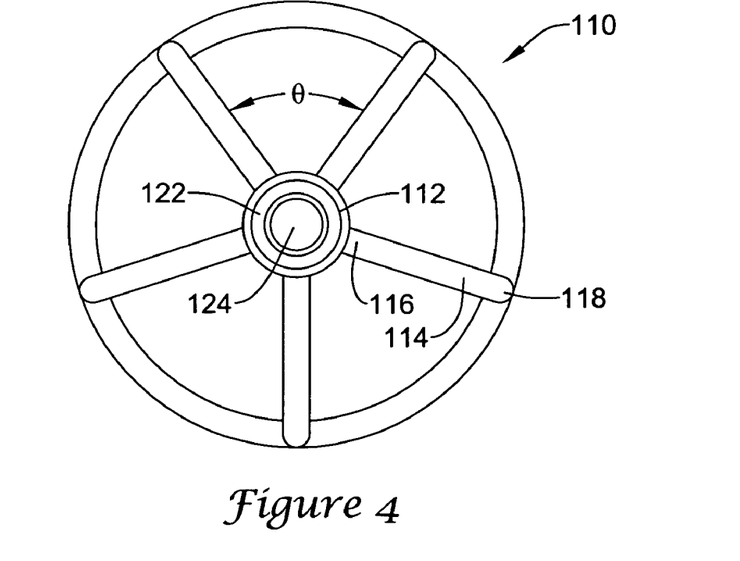
FIG. 4 is a top perspective view of the inflatable intravascular filter of FIG. 3.

FIG. 4 is a top perspective view of the inflatable intravascular filter 110 of FIG. 3. As shown in FIG. 4, the annular-shaped base member 128 can be configured to maintain each of the inflatable filter legs 114 at equidistant intervals θ (e.g. θ=72°) apart from each other, thereby maintaining the generally conical shape of the intravascular filter 110.

Figure 5:
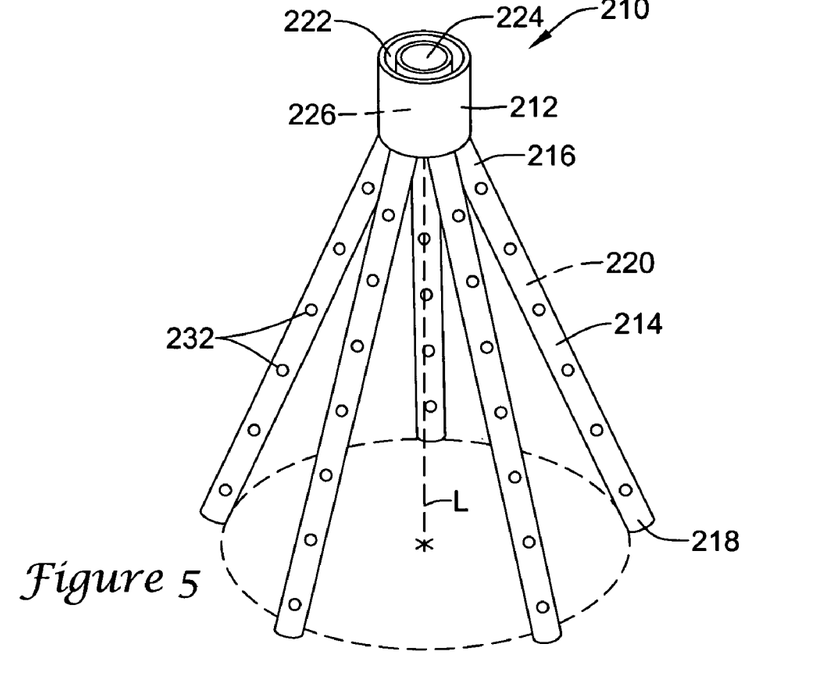
FIG. 5 is a perspective view of an inflatable intravascular filter including a number of perfusion openings.

FIG. 5 is a perspective view of an inflatable intravascular filter 210 in accordance with another illustrative embodiment of the present invention. Intravascular filter 210 can be configured similar to intravascular filter 10 described above, having an apical head 212 and one or more inflatable filter legs 214 actuatable between a radially collapsed position and a radially expanded position. Each of the inflatable filter legs 214 can include a first end section 216, a second end section 218, and an interior cavity 220 at least in part therethrough adapted to receive an inflation medium. As with other embodiments herein, the apical head 212 can include other features such as an inflation lumen 222, a guidewire lumen 224, and an internal valve mechanism 226. In the illustrative embodiment of FIG. 5, each inflatable filter leg 214 can further include one or more perfusion openings 232 that can be used to weep fluid into the bloodstream.

Figure 6:
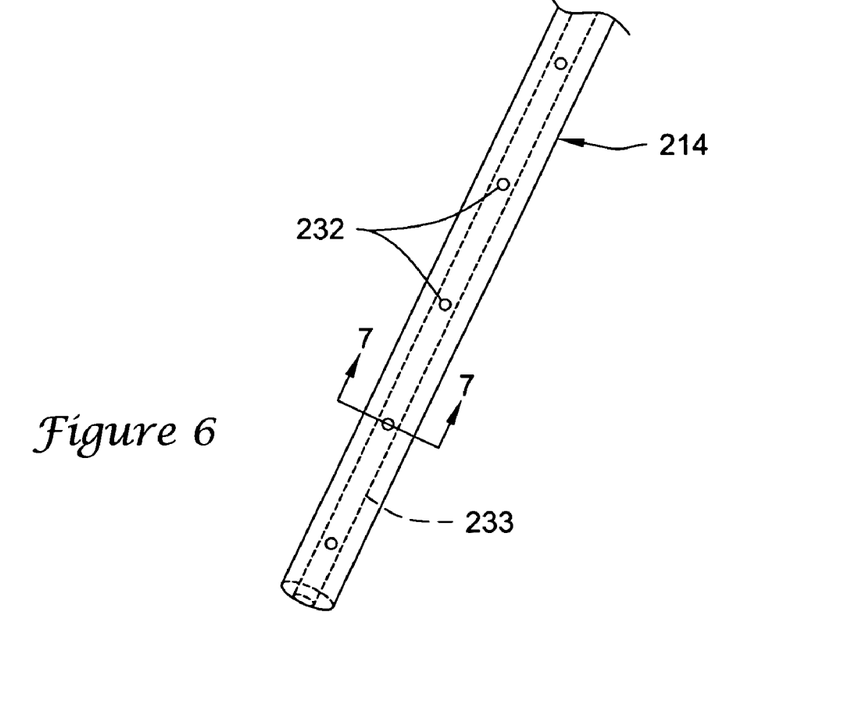
FIG. 6 is a detail view of an inflatable filter leg of the filter of FIG. 5.

FIG. 6 is a detailed view of an inflatable filter leg 214 of filter 210. Filter leg 210 includes a secondary cavity 233 within interior cavity 200. The secondary cavity 233 is in fluid communication with one or more perfusion openings 232. Fluid may weep from secondary cavity 233 from openings 232. That fluid may comprise an anti-coagulant drug that can be used to help prevent the formation of blood clots within the blood vessel. Examples of suitable anti-coagulants may include, but are not limited to, D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, tick anti-platelet peptides, or combinations thereof.

The number and size of the perfusion openings 232 can be selected to regulate the amount of inflation medium injected into the bloodstream over a period of time. In certain embodiments, for example, the perfusion openings 232 can be made relatively small to provide a lower rate of injection whereas relatively large perfusion openings 232 can be provided to produce a higher rate of injection. The material characteristics of the fluid and/or the pressure within the interior cavity 220 can also be varied to regulate the rate of injection into the bloodstream. In certain embodiments, for example, a gel-like fluid can be employed at relatively low pressures to produce a relatively slow rate of injection, allowing the intravascular filter 210 to remain rigid for a greater period of time before removal becomes necessary.

Figure 7:
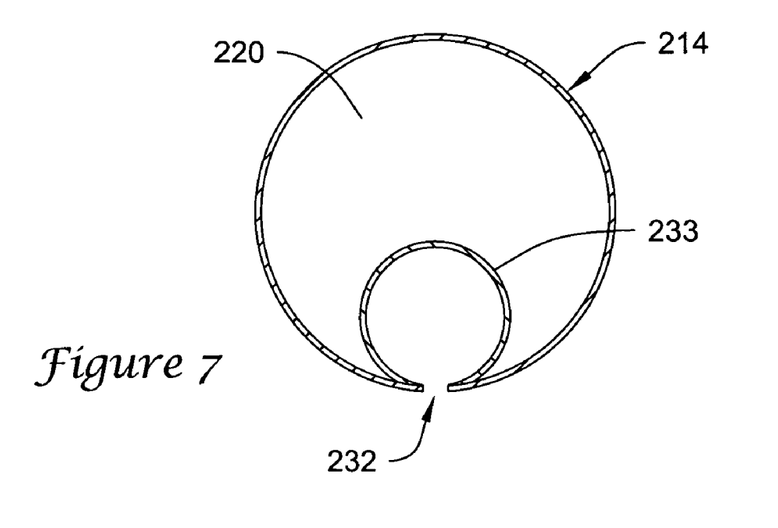
FIG. 7 is a cross-sectional view of the filter leg of FIG. 6.

FIG. 7 is a cross-sectional view of filter leg 214 of FIG. 6. As shown in FIG. 7 is interior cavity 220 and secondary cavity 233 contained therein.

Figure 8:
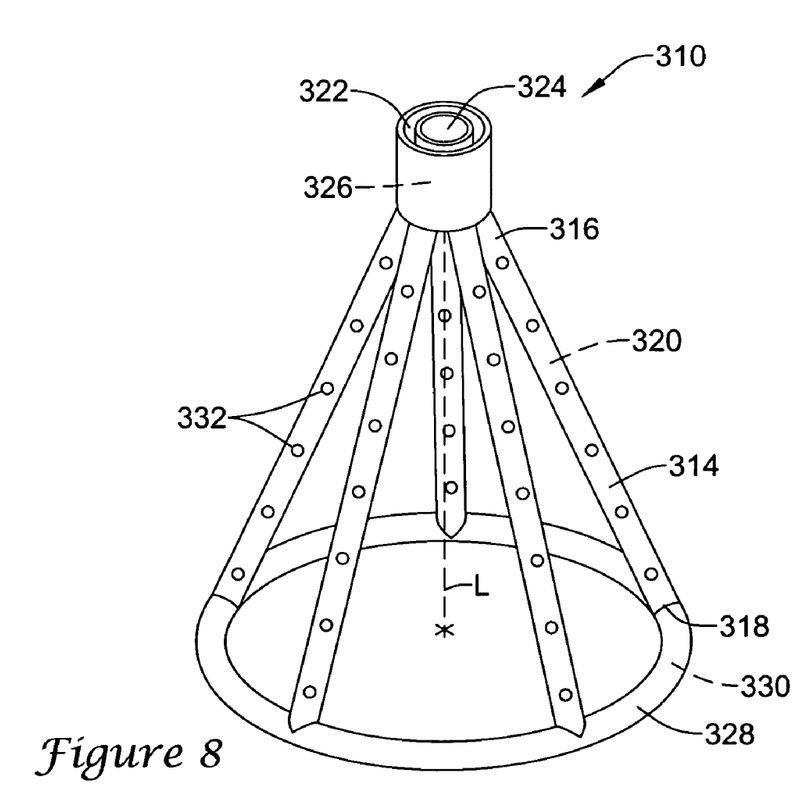
FIG. 8 is a perspective view of an inflatable intravascular filter including a number of perfusion openings and a base member.
Figure 9:
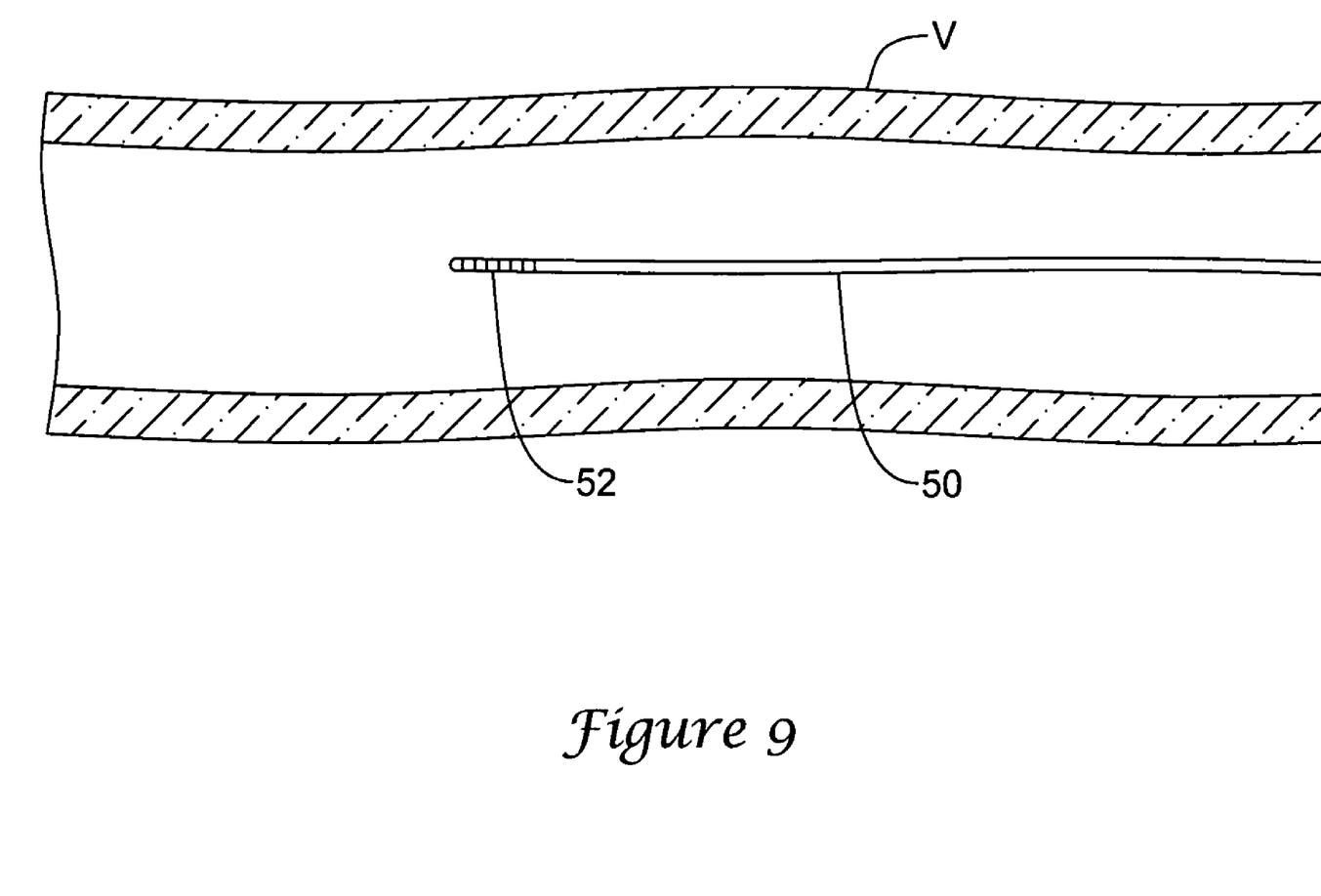
FIG. 9 is a partial cross-sectional view showing a guidewire inserted into a blood vessel.

FIG. 8 is a perspective view of an inflatable intravascular filter 310 in accordance with another illustrative embodiment of the present invention. Intravascular filter 310 can be configured similar to intravascular filter 110 described above, having an apical head 112 and one or more inflatable filter legs 314 actuatable between a radially collapsed position and a radially expanded position. Each of the inflatable filter legs 314 can include a first end section 316, a second end section 318, and an interior cavity 320 at least in part therethrough adapted to receive an inflation medium. As with other embodiments herein, the apical head 312 can include other features such as an inflation lumen 322, a guidewire lumen 324, and an internal valve mechanism 326.

As can be further seen in FIG. 8, each of the inflatable filter legs 314 can be coupled to or formed integrally with an annular-shaped base member 328 that can be used to provide further structural support to the intravascular filter 310, if desired. The annular-shaped base member 328 can comprise an inflatable extension of the material forming the inflatable filter legs 314, or cam comprise a separate member that is attached to each of the inflatable filter legs 314. As shown in the illustrative embodiment of FIG. 6, for example, the base member 328 can define an interior cavity 330 in fluid communication with the interior cavity 320 of each inflatable filter leg 314, allowing the base member 328 to be inflated and/or deflated via the apical head 312. In other embodiments, however, the base member 328 can comprise a non-inflatable member such as a wire, tube, coil, or the like.

Turning now to FIGS. 9-13, an illustrative method of filtering blood clots contained within a blood vessel will now be described with respect to intravascular filter 310. In a first position depicted in FIG. 9, a guidewire 50 having a distal end 52 is shown inserted into a blood vessel V. Placement of the guidewire 50 can accomplished percutaneously via one of the femoral arteries or via the jugular vein in accordance with standard practice in the art. The manner of inserting the guidewire within the blood vessel V will, of course, vary depending on the particular location in which the intravascular filter 310 is to be inserted. In some embodiments, for example, it may be desirable to place the intravascular filter 310 within the inferior vena cava for the treatment of Deep Vein Thrombosis (DVT). In such cases, it may be desirable to use a guide catheter or other guiding member to facilitate insertion of the guidewire 50 through tortuous regions of the vasculature (e.g. the aortic arch).

Figure 10:
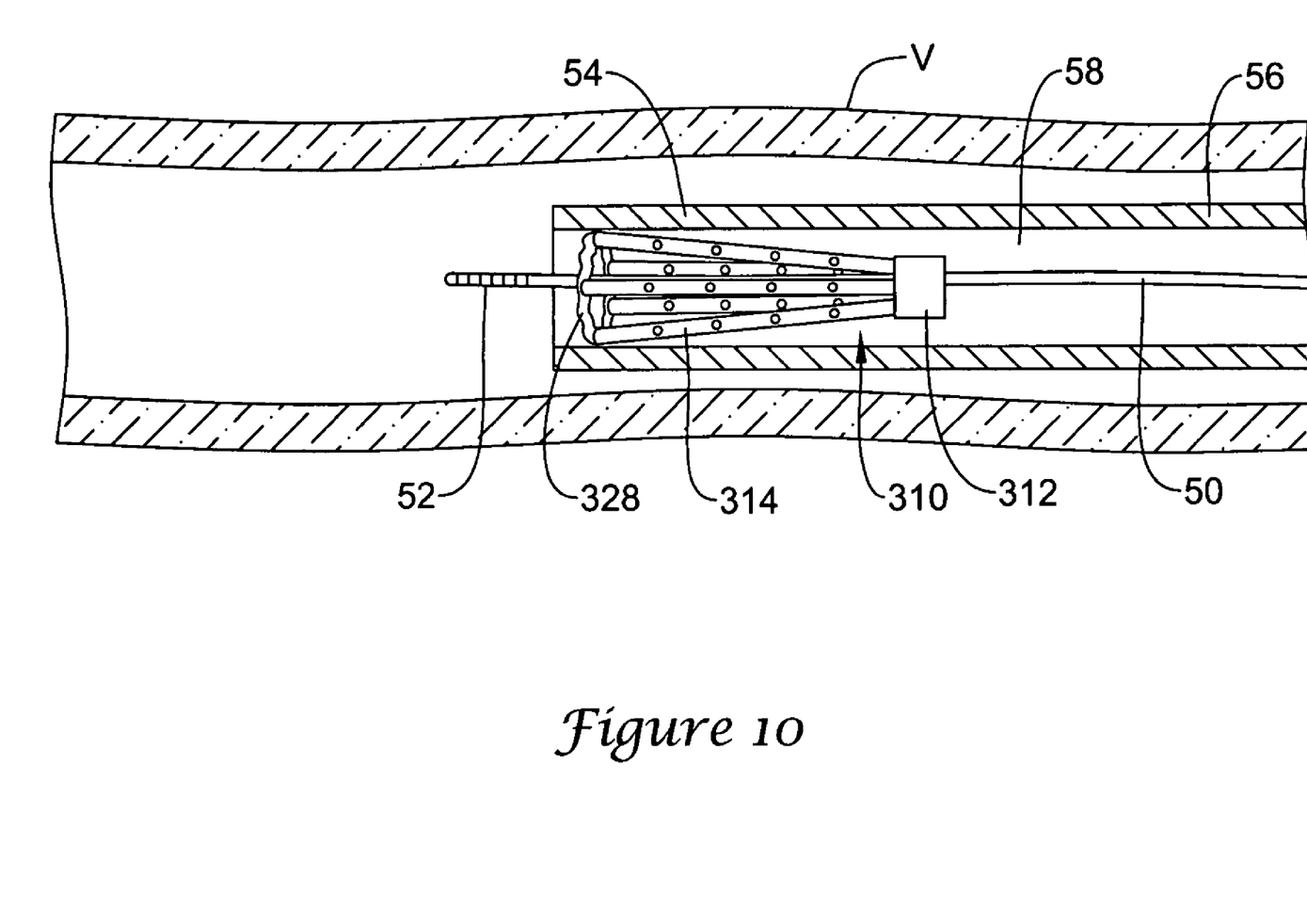
FIG. 10 is a partial cross-sectional view showing the intravascular filter of FIG. 6 loaded into a sheath and advanced distally along the guidewire of FIG. 9.

With the guidewire 50 placed within the blood vessel V, the physician may next advance the intravascular filter 310 along the guidewire 50 to a desired implantation site, as shown, for example, in FIG. 10. As can be seen in FIG. 10, the intravascular filter 310 can be loaded into the distal end 54 of a sheath 56 or other suitable delivery means, and then advanced along the guidewire 50 to a location proximal the distal end 52 thereof. The sheath 56 may define an inner lumen 58 dimensioned to transport the intravascular filter 310 in a deflated (i.e. collapsed) position within the vasculature.

Figure 11:
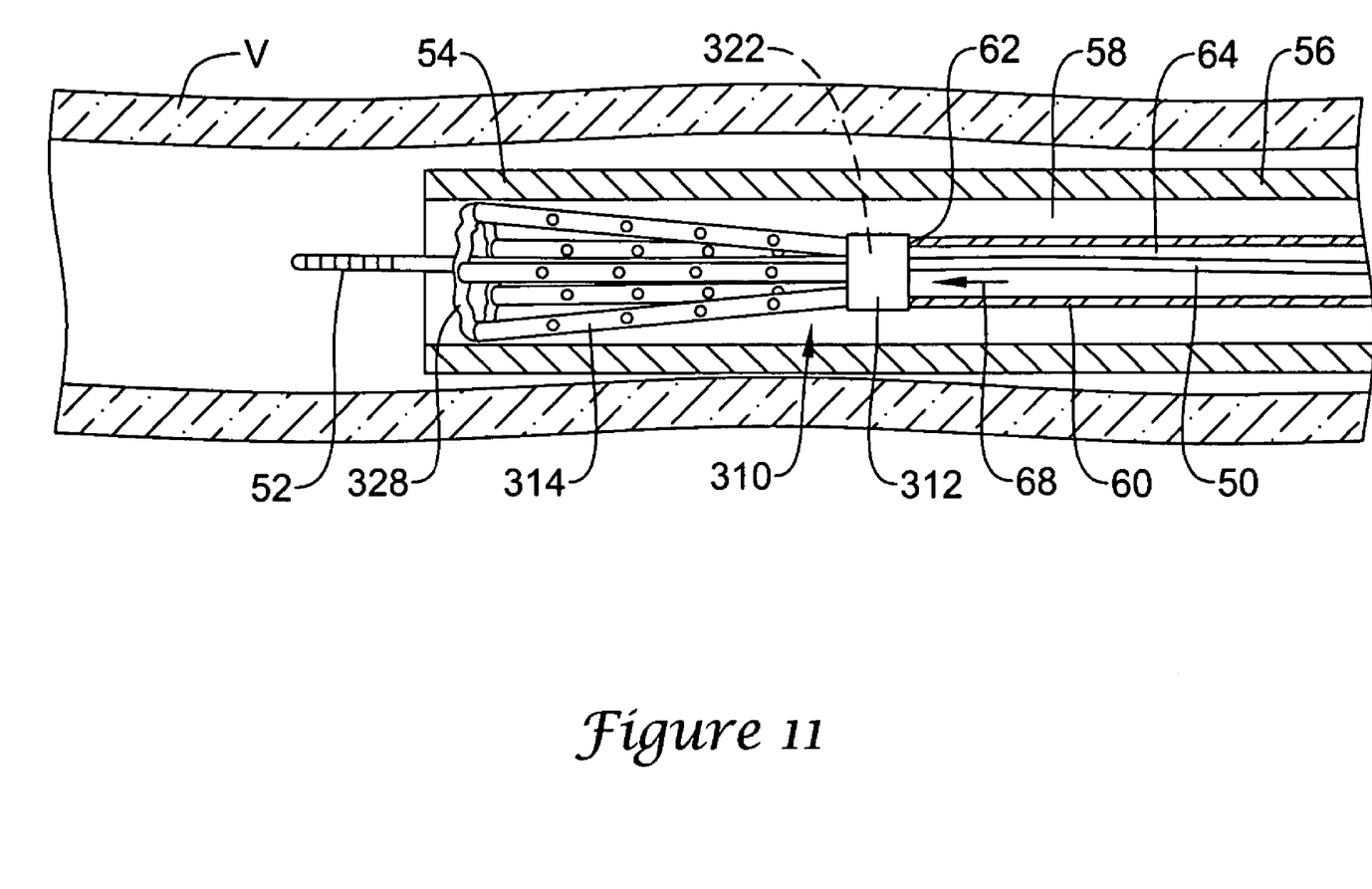
FIG. 11 is a partial cross-sectional view showing an inflation catheter advanced to the site of the intravascular filter of FIG. 10.

To expand the intravascular filter 310 within the blood vessel V, an inflation catheter 60 can be advanced along the guidewire 50 to a position immediately adjacent and proximal to the apical head 312, as shown, for example, in FIG. 11. The inflation catheter 60 can include a proximal end (not shown), a distal end 62, and an inflation lumen 64 in fluid communication with an inflation source. As can be seen in FIG. 11, the distal end 62 of the inflation catheter 60 can be configured to seal tightly against the apical head 312, allowing inflation medium 68 within the inflation lumen 64 to be injected through the inflation lumen 322 and into the inflatable filter legs 314 and base member 328.

Figure 12:
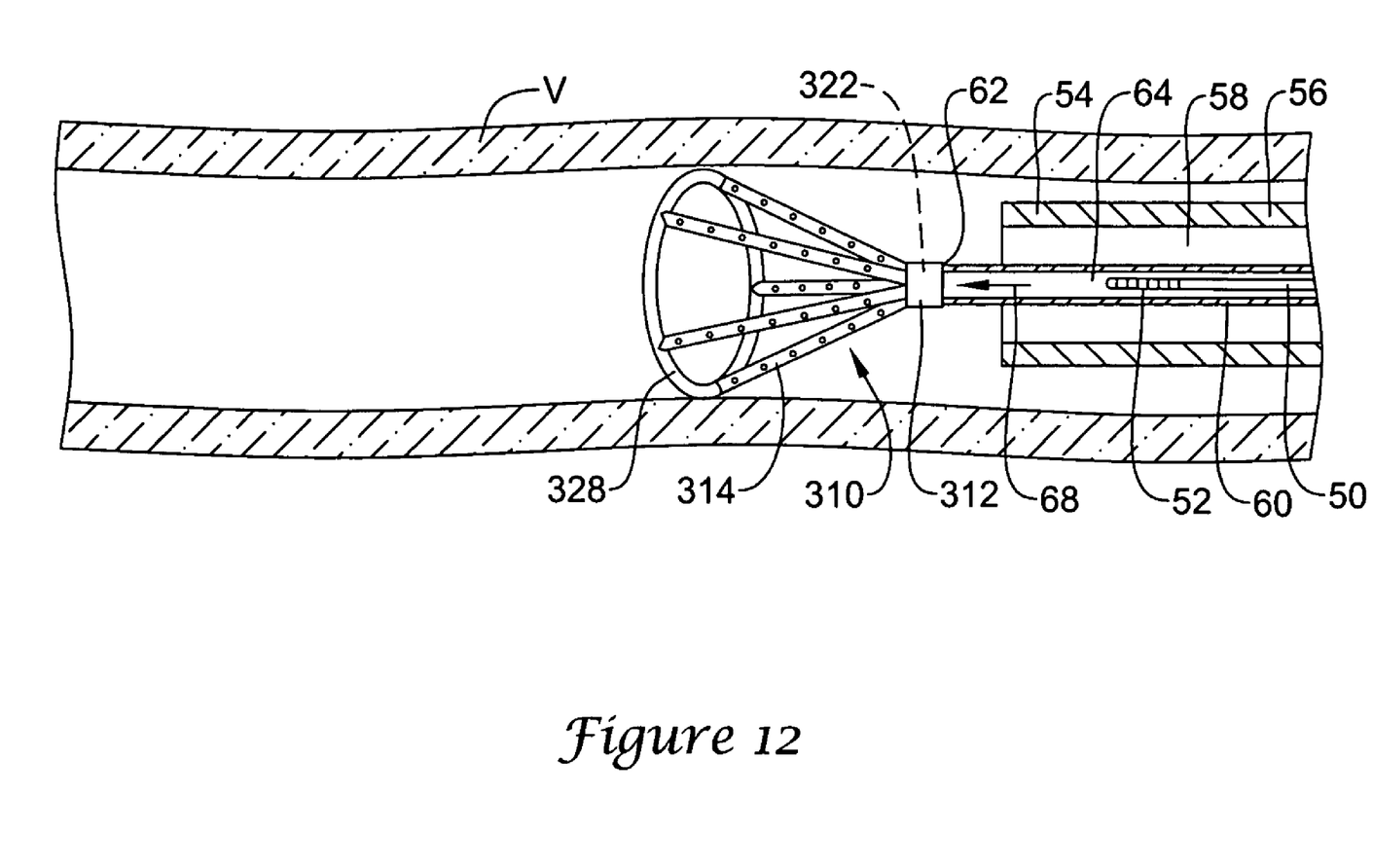
FIG. 12 is a partial cross-sectional view showing the inflation of the intravascular filter within the blood vessel.

To deploy the intravascular filter 310 within the blood vessel V, the sheath 56 can be withdrawn proximally while inflation medium 68 within the inflation catheter 60 is injected into the intravascular filter 310, as shown, for example, in FIG. 12. In an alternative technique, the sheath 56 can be held stationary while advancing the inflation catheter 60 in the distal direction, similarly causing the intravascular filter 310 to deploy. Once the intravascular filter 310 has been deployed in the blood vessel V, the physician may then remove the guidewire 50, sheath 56, and inflation catheter 60 from the patient's body, if desired.

Figure 13:
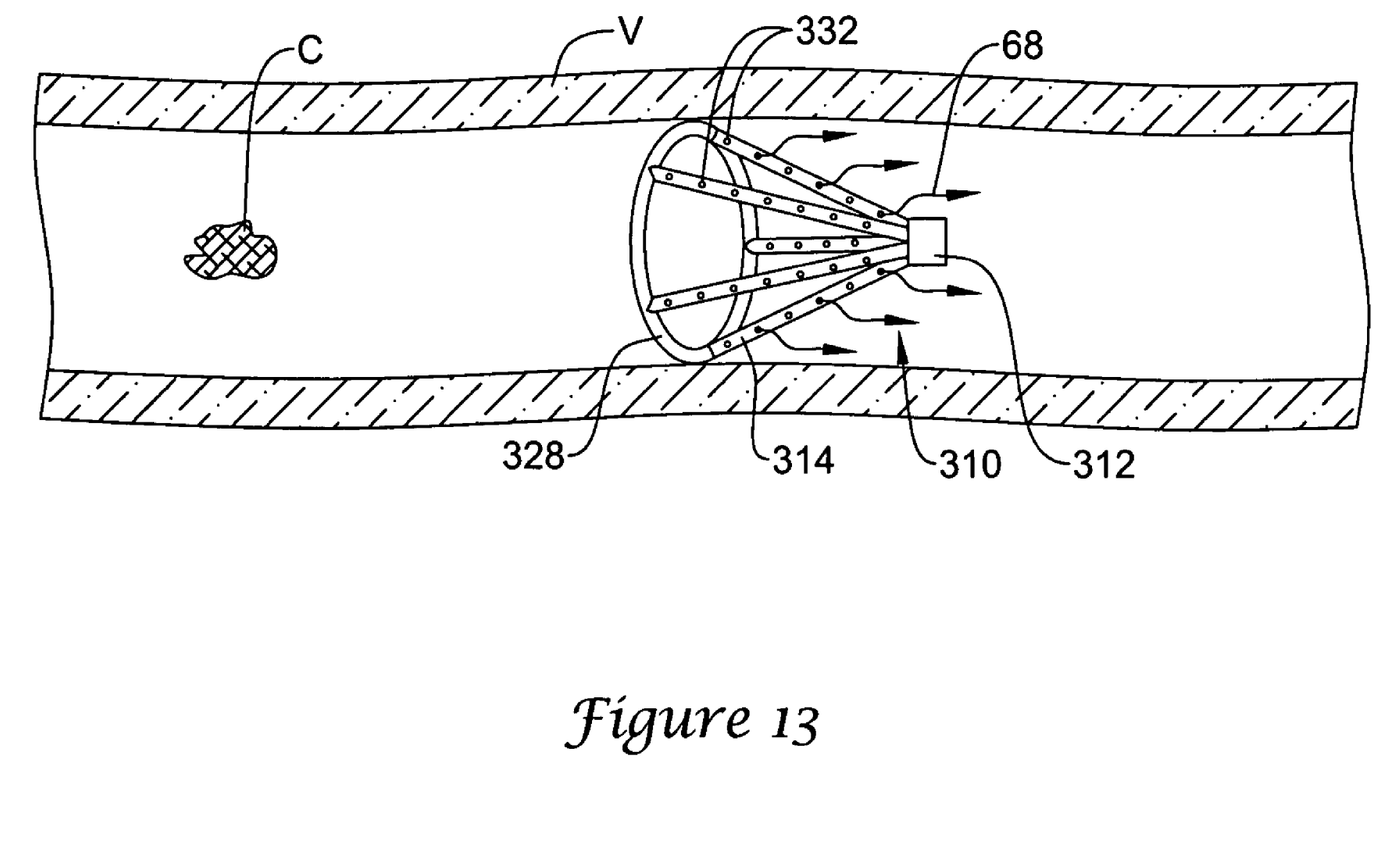
FIG. 13 is a partial cross-sectional view showing the intravascular filter in a fully expanded position within the blood vessel.

In use, the intravascular filter 310 can be configured to collect and lyse blood clots contained within the blood vessel V. As shown in FIG. 13, for example, in those embodiments including perfusion openings 332, a small amount of inflation medium 68 can be injected into the blood stream to therapeutically treat the patient while maintaining the generally rigid shape of the intravascular filter 310. In certain embodiments, for example, the inflation medium 68 can include an anti-thrombogenic and/or anti-inflammatory agent to prevent further thrombosis formation within the blood vessel V, and to reduce inflammation caused by the intravascular filter 310. The inflation medium 68 can also include anti-coagulant drugs to prevent the further formation of blood clots within the blood vessel V.

To remove the intravascular filter 310 from the blood vessel V, the physician may advance the sheath 56 and inflation catheter 60 to the site of the intravascular filter 310, and then re-engage the inflation catheter 60 against the apical head 312 to deflate the inflatable filter legs 314 and base member 328. In certain embodiments, a suction force can be applied to deflate the intravascular filter 310. Alternatively, the action of advancing the distal end 62 of the inflation catheter 60 against the apical head 312 can be configured to deflate the intravascular filter 310. Once the inflatable filter legs 314 and member 328 are at least partially deflated, the intravascular filter 310 can then be retracted into the interior lumen 58 of the sheath 56 to a position similar to that depicted in FIG. 10. The retrieval sheath and accompanying intravascular filter 310 can then be removed from the patient's body or redeployed in a different location of the vasculature, as desired.

Having thus described the several embodiments of the present invention, those of skill in the art will readily appre- ciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An inflatable intravascular filter, comprising:
   an apical head;
   one or more inflatable filter legs operatively coupled to the apical head, each inflatable filter leg including a first end section, a second end section, and an interior cavity,
   wherein the apical head includes a one-way valve mechanism in fluid communication with the interior cavity; and
   wherein the one-way valve mechanism includes a releasable connection to connect to an inflation catheter.

2. The intravascular filter of claim 1, wherein each inflatable filter leg comprises an elongated tubular member.

3. The intravascular filter of claim 1, further comprising a base member coupled to or formed integrally with the second end section of each inflatable filter leg.

4. The intravascular filter of claim 3, wherein said base member is an inflatable member.

5. The intravascular filter of claim 1, wherein the intravascular filter is actuatable between a radially collapsed position and a radially expanded position.

6. The intravascular filter of claim 1, further comprising an inflation medium disposed within the interior cavity.

7. The intravascular filter of claim 6, wherein at least one inflatable filter leg includes one or more perfusion openings adapted to weep inflation medium therefrom.

8. The intravascular filter of claim 7, wherein said inflation medium includes an anti-coagulant drug.

9. An inflatable intravascular filter, comprising:
   an apical head one or more inflatable filter legs operatively coupled to the apical head and actuatable between a radially collapsed position and a radially expanded position, each inflatable filter leg including a first end section, a second end section, and an interior cavity;
   a base member coupled to or formed integrally with the second end section of each inflatable filter leg,
   wherein the apical head includes a one-way valve mechanism in fluid communication with the interior cavity; and
   wherein the one-way valve mechanism includes a releasable connection to connect to an inflation catheter.

10. The intravascular filter of claim 9, wherein each inflatable filter leg comprises an elongated tubular member.

11. The intravascular filter of claim 9, wherein said base member is an inflatable member.

12. The intravascular filter of claim 9, further comprising an inflation medium disposed within the interior cavity.

13. The intravascular filter of claim 12, wherein at least one inflatable filter leg includes one or more perfusion openings adapted to weep inflation medium therefrom.

14. The intravascular filter of claim 13, wherein said inflation medium includes an anti-coagulant drug.

15. A filter system, comprising:
    an inflatable intravascular filter including an apical head and one or more inflatable filter legs operatively coupled to the apical head, each inflatable filter leg including a first end section, a second end section, and an interior cavity adapted to receive an inflation medium;
    an inflation catheter for injecting inflation medium into the interior cavity of said one or more inflatable filter legs,
    wherein the apical head includes a one-way valve mechanism configured to prevent escape of the inflation medium from the interior cavity; and
    wherein the one-way valve mechanism includes a releasable connection to connect to an inflation catheter.

16. The filter system of claim 15, further comprising a base member coupled to or formed integrally with the second end section of each inflatable filter leg.

17. The filter system of claim 16, wherein said base member is an inflatable member.

18. The filter system of claim 15, wherein the intravascular filter is actuatable between a radially collapsed position and a radially expanded position.

19. The filter system of claim 15, wherein at least one inflatable filter leg includes one or more perfusion openings adapted to weep inflation medium therefrom.

20. The filter system of claim 15, wherein said inflation medium includes an anti-coagulant drug.

21. The filter system of claim 15, wherein said inflation catheter includes a proximal end, a distal end, and an inflation lumen.

22. A method of filtering blood clots contained within a blood vessel, comprising the steps of:
    providing an inflatable intravascular filter including an apical head and one or more inflatable filter legs operatively coupled to the apical head, each inflatable filter leg including a first end section, a second end section, and an interior cavity adapted to receive an inflation medium;
    wherein the apical head includes a one-way valve mechanism configured to prevent escape of the inflation medium from the interior cavity;
    wherein the one-way valve mechanism includes a releasable connection to connect to an inflation catheter;
    advancing the intravascular filter in a deflated position to a target location within the blood vessel;
    inflating the intravascular filter and causing the one or more inflatable filter legs to expand and engage the wall of the blood vessel; and
    collecting blood clots contained within the blood vessel.

23. The method of claim 22, wherein the step of advancing the intravascular filter to a target location within the blood vessel includes the step of loading the intravascular filter into a sheath.

24. The method of claim 22, wherein the step of inflating the intravascular filter and causing the one or more inflatable filter legs to expand and engage the wall of the blood vessel includes the steps of:
    providing an inflation catheter having a proximal end, a distal end, and an inflation lumen;
    advancing the inflation catheter to the site of the intravascular filter and engaging a valve mechanism of the apical head; and
    injecting an inflation medium into the intravascular filter.

25. The method of claim 22, wherein at least one inflatable members includes one or more perfusion openings, and further including the step of weeping inflation medium into the blood vessel.

26. The method of claim 22, further comprising the step of removing the intravascular filter from the blood vessel.

* * * * *